US008822953B2

(12) United States Patent
Shibuya et al.

(10) Patent No.: US 8,822,953 B2
(45) Date of Patent: Sep. 2, 2014

(54) ELECTRON BEAM IRRADIATION APPARATUS

(71) Applicant: Shibuya Kogyo Co., Ltd., Ishikawa (JP)

(72) Inventors: Hirotoshi Shibuya, Ishikawa (JP); Toshiaki Naka, Ishikawa (JP); Yukinobu Nishino, Ishikawa (JP); Ryo Abe, Ishikawa (JP); Tokuo Nishi, Ishikawa (JP); Yukihiro Yamamoto, Ishikawa (JP)

(73) Assignee: Shibuya Kogyo Co., Ltd., Kanazawa-Shi, Ishikawa (JP)

( * ) Notice: Subject to any disclaimer, the term of this patent is extended or adjusted under 35 U.S.C. 154(b) by 0 days.

(21) Appl. No.: 13/775,812

(22) Filed: Feb. 25, 2013

(65) Prior Publication Data

US 2013/0221244 A1  Aug. 29, 2013

(30) Foreign Application Priority Data

Feb. 28, 2012  (JP) ................................. 2012-042203

(51) Int. Cl.
   *A61L 2/08*  (2006.01)
   *G21K 5/00*  (2006.01)
   *H01J 33/04*  (2006.01)

(52) U.S. Cl.
   CPC . *A61L 2/087* (2013.01); *G21K 5/00* (2013.01); *H01J 33/04* (2013.01)
   USPC .................. 250/453.11; 250/492.1; 250/492.3

(58) Field of Classification Search
   CPC ............ A61L 2/08; A61L 2/087; G21K 5/00; G21K 5/04; G21K 5/08; G21K 5/10; H01J 37/30; H01J 37/3002; H01J 37/301; H01J 5/18

USPC ................. 250/453.11, 455.11, 492.1, 492.3
   See application file for complete search history.

(56) References Cited

U.S. PATENT DOCUMENTS

| 2003/0089852 | A1* | 5/2003 | Ochiai et al. ................... 250/310 |
| 2009/0110613 | A1* | 4/2009 | Naka et al. ..................... 422/186 |
| 2010/0072395 | A1* | 3/2010 | Nishino et al. ........... 250/455.11 |
| 2010/0140507 | A1* | 6/2010 | Nishino et al. ............. 250/491.1 |
| 2010/0326563 | A1* | 12/2010 | Kobayashi et al. ............. 141/11 |
| 2011/0096895 | A1* | 4/2011 | Kurochi .......................... 378/19 |

FOREIGN PATENT DOCUMENTS

| JP |   03-015421 U   |   | 2/1991 |
| JP |    09211199 A   | * | 8/1997 |
| JP |   2010-008387   |   | 1/2010 |
| JP |   2010008387 A  | * | 1/2010 |

\* cited by examiner

*Primary Examiner* — Jack Berman
*Assistant Examiner* — David E Smith
(74) *Attorney, Agent, or Firm* — Greenblum & Bernstein, P.L.C.

(57) ABSTRACT

An electron beam irradiation apparatus is provided that includes a vacuum room, an electron beam generator, a window frame, and an irradiation foil. The vacuum room includes a wall having an opening through which an electron beam is irradiated. An internal atmosphere of the vacuum room is evacuated. The electron beam generator is provided inside the vacuum room. The window frame is attached to and surrounds the opening in the wall of the vacuum room. The irradiation foil, through which an electron beam generated in the vacuum room is transmitted, is fixed to the window frame. The surface of the window frame, at least an area exposed to the vacuum room, is substantially covered with material including an element or elements with an atomic number less than or equal to 10.

9 Claims, 5 Drawing Sheets

ELECTRON BEAM IRRADIATION APPARATUS

BACKGROUND OF THE INVENTION

1. Field of the Invention

The present invention relates to an electron beam irradiation apparatus that irradiates an article (an irradiated object) with an electron beam in a disinfection or similar process, and specifically to an electron beam irradiation apparatus that is able to reduce the amount of X-rays generated by electron beam irradiation.

2. Description of the Related Art

An electron beam generator carries out a disinfection process by emitting an electron beam through a window toward an article being transported by a conveyor system. It is generally known that X-rays are generated when electrons emitted from an electron beam irradiation apparatus collide with metallic members inside a disinfection room where the conveyor system is installed. An invention that reduces the above-discussed generation of X-rays (e.g., Japanese Utility Model Application Laid-Open Publication H03-015421) and an invention that shields the X-rays from leakage (e.g., Japanese Patent Application Laid-Open Publication 2010-008387) have already been provided.

The invention described in Japanese Utility Model Application Laid-Open Publication H03-015421 disposes a beam catcher in a position facing the electron beam irradiation apparatus, which emits electron beams. A surface of the beam catcher on the electron radiation side is covered with aluminum and configured as an aluminum plate shielded with a PE (polyethylene) cover.

Further, in the invention described in Japanese Patent Application Laid-Open Publication 2010-008387, the entire irradiation room is configured to shield X-rays and an X-ray shield structure is further provided to surround an irradiating space inside the irradiation room and the beam catcher.

SUMMARY OF THE INVENTION

The inventions described in the above-mentioned documents are designed to control only X-rays generated within a space in which an article is being irradiated by an electron beam in a disinfection process; X-rays generated inside the vacuum chamber housing the source of the electron beam are disregarded. However, X-rays are also generated in a vacuum room when an electron beam strikes metal. In this situation, an electron beam generated in a vacuum room is emitted toward an external processing area through irradiation foil in a window frame that is fitted to an opening provided on a wall inside the chamber. The trajectory of the electron beam is generally straight but some electrons collide with the window frame and the wall that supports the window frame. Therefore, X-rays are also generated in the vacuum chamber. Accordingly, the entire system is covered with lead material to prevent the X-rays from leaking outside. In order to prevent leakage of the X-rays the system should be covered with thick lead members, which increase the cost of the system.

The present invention considers the above-mentioned issues, thus one aspect of the present invention is to provide an electron beam irradiation apparatus that is able to reduce not only X-rays generated within a space for irradiating an article with electron beams, but also in a vacuum chamber where the electron beams are produced.

According to a primary aspect of the present invention, an electron beam irradiation apparatus is provided that includes a vacuum room, an electron beam generator, a window frame, and irradiation foil.

The vacuum room includes a wall having an opening through which an electron beam is radiated. An internal atmosphere of the vacuum room is evacuated. The electron beam generator is provided inside the vacuum room. The window frame is attached to and surrounds the opening in the wall of the vacuum room. The irradiation foil through which an electron beam generated in the vacuum room is transmitted is fixed to the window frame. The surface of the window frame, at least an area exposed to the vacuum room, is substantially covered with material including an element or elements with an atomic number less than or equal to 10.

According to another aspect of the present invention, a beam catcher for receiving an irradiated electron beam is further provided on the opposite side of the irradiation foil with respect to an irradiated object and a surface of the beam catcher is substantially covered with a material including an element or elements with an atomic number less than or equal to 10.

According to another aspect of the present invention, a surface of an inner wall about the opening of the vacuum room is covered with material including an element or elements with an atomic number less than or equal to 10.

According to another aspect of the present invention, the material includes at least one of carbon and fluorine as its main element.

According to another aspect of the present invention, the material includes carbon fiber reinforced plastic.

According to another aspect of the present invention, the window frame includes copper and an area of the window frame facing inside the vacuum room is covered with carbon-fiber-reinforced plastic.

According to another aspect of the present invention, the window frame is provided with a plurality of crosspiece sections aligned in parallel along one direction and each of the opposing surfaces of the crosspiece sections is covered with carbon-fiber-reinforced plastic.

Accordingly, since the surface of the window frame, which is attached to the opening of the vacuum room on the side facing or exposed to the electron beam generator, is covered with material including an element or elements with an atomic number less than or equal to 10, the inventive electron beam irradiation apparatus can significantly reduce the X-rays generated within the vacuum chamber.

BRIEF DESCRIPTION OF THE DRAWINGS

The objects and advantages of the present invention will be better understood from the following description with references to the accompanying drawings in which.

DESCRIPTION OF THE PREFERRED EMBODIMENTS

Figure 1:
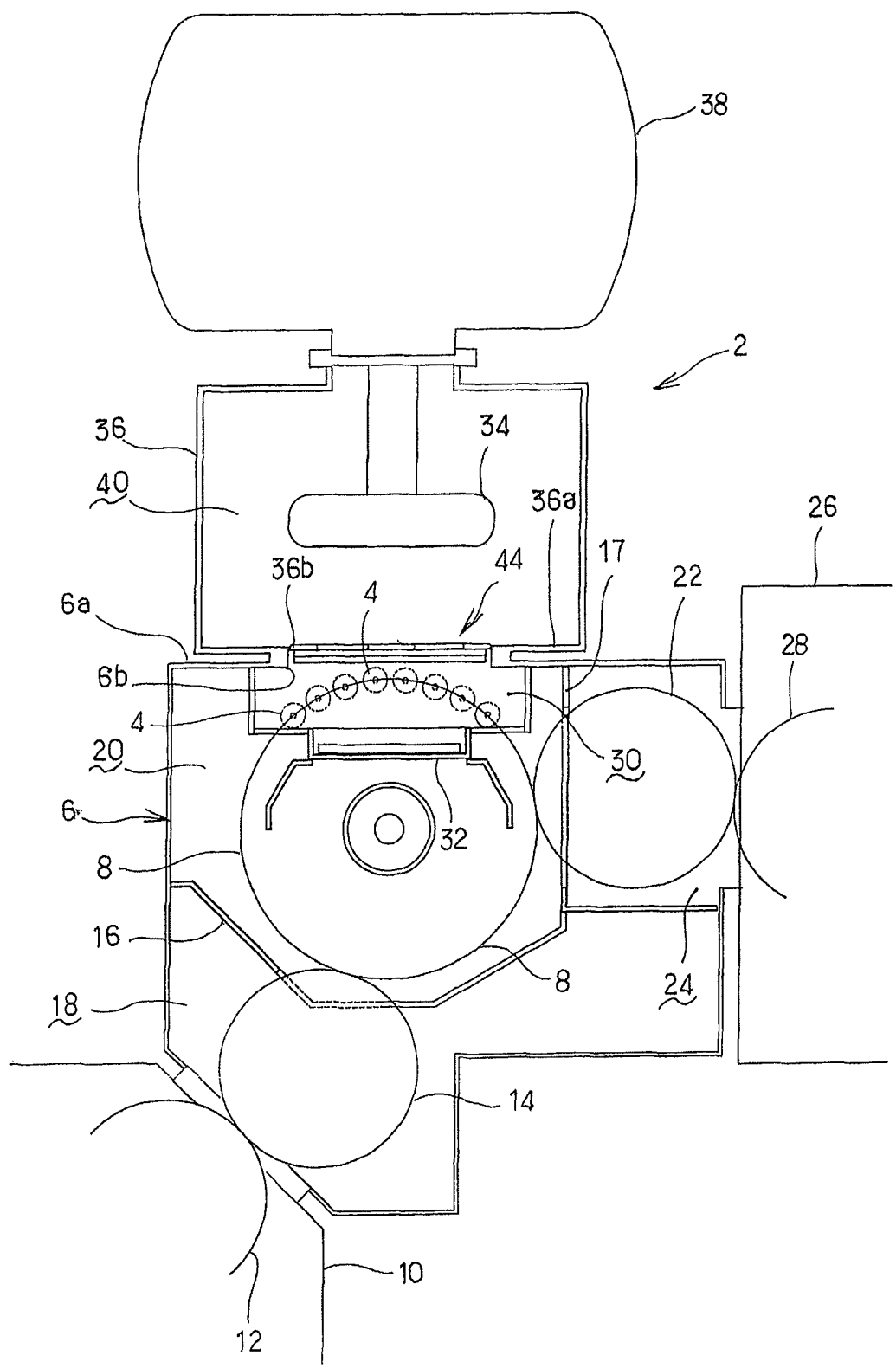
FIG. 1 is a plan view of an electron beam disinfection apparatus provided with the inventive electron beam irradiation apparatus.

The present invention is described below with references to the embodiments shown in the drawings.

An electron beam irradiation apparatus 2 of the present embodiment receives resin-made containers (irradiated objects) 4, such as PET bottles and the like, which are conveyed from the outside into a disinfection chamber 6, and disinfects the containers 4 by irradiating them with electron beams as they are carried in a circular direction by a rotary conveyor 8. The sterilized containers 4 are then transferred to a filling and capping line, such as to a filler and capper.

The containers 4, which will be irradiated by electron beams from the electron beam irradiation apparatus 2, may be transferred by a transfer system such as an air conveyor (not shown), and are carried into an installation chamber 10 disposed on the upstream side of the disinfection chamber 6 for the sterilization. Inside the installation chamber 10, a carry-in wheel 12 is provided. The carry-in wheel 12 has grippers (not shown) at regular intervals along its circumference for gripping the containers 4. The containers 4, which are transported into the installation chamber 10, are handed over to the grippers of the carry-in wheel 12 and transported in a circular direction.

The disinfection chamber 6 is disposed next to the installation chamber 10. A connecting portion between the installation chamber 10 and the disinfection chamber 6 is provided with an opening that is used to transfer the containers 4 between the carry-in wheel 12 of the installation chamber 10 and a supply wheel 14 disposed inside the disinfection chamber 6 near the opening. The disinfection chamber 6 is divided into separate rooms by partition walls 16 and 17, such as an entrance room 18 where the supply wheel 14 is disposed, a main room where a transfer system (a transfer wheel) 8 is disposed, and an exit room 24 where a discharge wheel 22 is disposed. Each of the supply wheel 14, the transfer wheel 8 and the discharge wheel 22 are also provided with grippers (not shown) at regular intervals along each periphery for gripping the container 4, so that the containers 4 are transferred between the grippers one after the other. The disinfection chamber 6 and the partition walls 16 and 17 inside the disinfection chamber 6 may be made of a leaden wall (in this embodiment, a leaden plate may be sandwiched between stainless steel plates) to shield X-rays (Bremsstrahlung X-rays) and electron beams to prevent their leakage to the outside when the containers 4 are sterilized by irradiation of electron beams. Note that each of the partition wall 16, between the entrance room 18 and the main room 20, and the partition wall 17, between the main room 20 and the exit room 24, has an opening for transferring the container 4 from one wheel to another.

A filling chamber 26 is disposed on a downstream side of the disinfection chamber 6 so that sterilized containers 4 are transferred from the discharge wheel 22 to a carry-out wheel 28 installed inside the filling chamber 26 and are fed to a filler, not shown.

A sidewall 6a (an upper side wall in FIG. 1) of the main room 20 where the transfer wheel 8 of the disinfection chamber 6 is installed has an opening 6b. The electron beam irradiation apparatus 2 is attached to the disinfection chamber 6 outside the opening 6b. Inside the disinfection chamber 6, a disinfection room 30 surrounds the opening 6b where the electron beam irradiation apparatus 2 is attached. A part of the transfer route of the containers 4 on the transfer wheel 8 passes through the disinfection room 30. While the containers 4 pass through the disinfection room 30, they are irradiated by electron beams from the electron beam irradiation apparatus 2, thus disinfection is performed.

Figure 5:
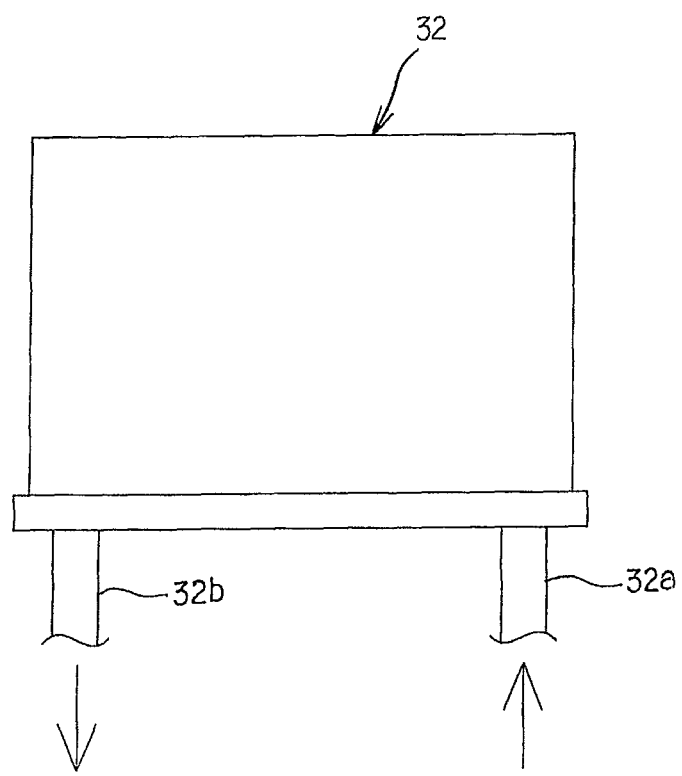
FIG. 5 is a front view of a beam catcher provided in the electron beam irradiation apparatus.

Inside the disinfection room 30, a beam catcher 32 for capturing any electron beams that pass through without irradiating the transferring container 4 is disposed on the opposite side of the electron beam irradiation apparatus 2 with respect to the path of the containers. Inside the beam catcher 32 there is provided a channel (not shown) for coolant as shown in FIG. 5. The coolant is supplied from an inlet pipe 32a and discharged from an outlet pipe 32b so that it is circulated inside the beam catcher 32 to prevent overheating caused by the electron beam irradiation process.

The electron beam apparatus 2 includes an electron beam generator 34 for generating an electron beam, an accelerating tube 36 for accelerating an electron beam generated by the electron beam generator 34 in a vacuum space (an accelerating space), and a power boost unit 38 connected to the electron beam generator 34. The features of the electron beam generator 34 are not depicted because it is well known in the art; however, the electron beam generator includes a linear filament for emitting a thermo electron, a gantry structure supporting the filament, and a grid to control the thermo electron generated by the filament. The filament is heated and generates thermo electrons that are transformed into an electron beam when high voltage is applied to accelerate the electrons in a vacuum cell 40 inside of the accelerating tube 36. The electron beam is emitted into the disinfection room 30 through metal foil covering an emission window 44, which will be detailed later. Note that outer surfaces of the accelerating tube 36 and the power boost unit 38 are also shielded by walls similar to those of the disinfection chamber 6, walls in which a lead plate is sandwiched between stainless steel plates.

Figure 2:
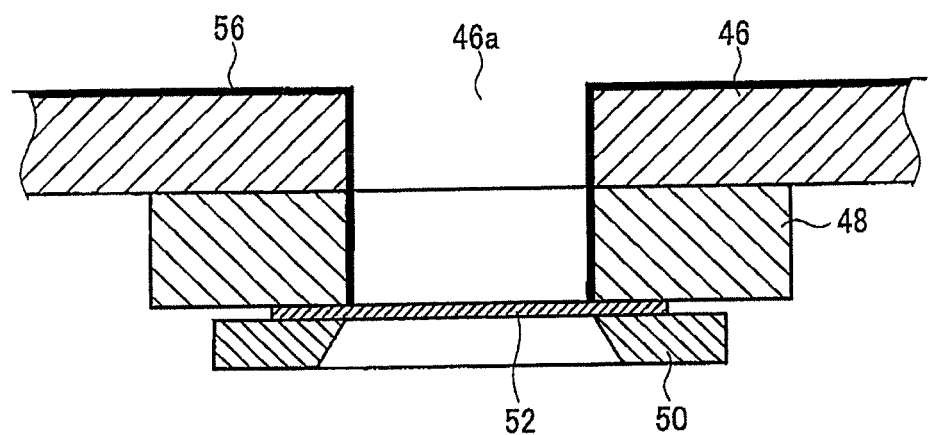
FIG. 2 is a cross-sectional view of an irradiation window provided in the electron beam irradiation apparatus.
Figure 3:
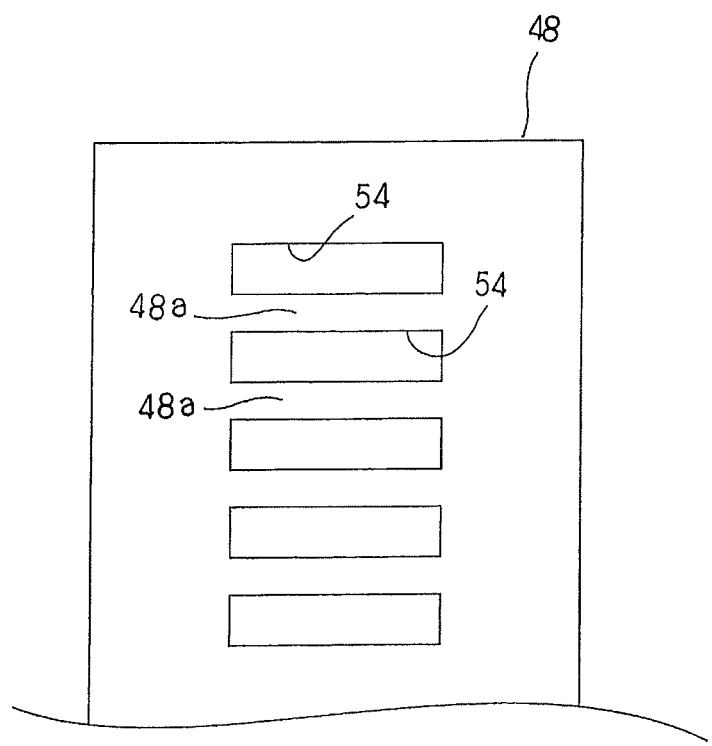
FIG. 3 is a front view of a window frame provided in the electron beam irradiation apparatus.
Figure 4:
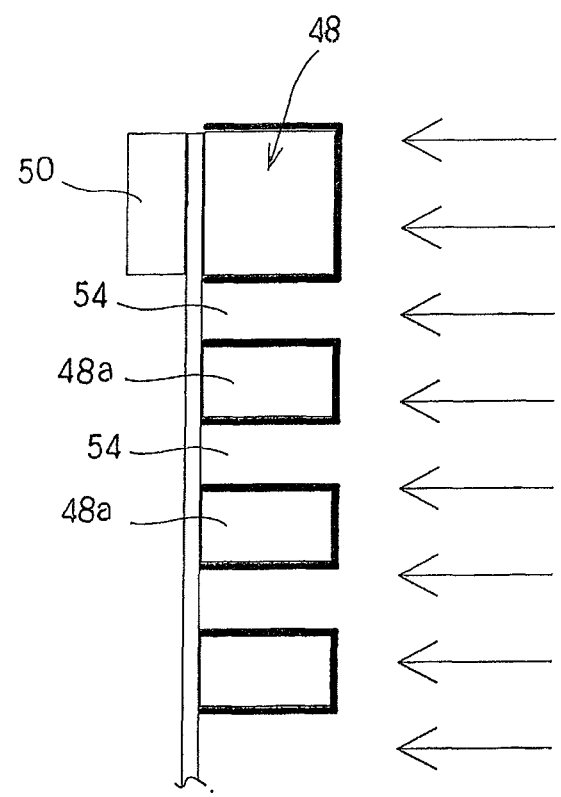
FIG. 4 is an elevated sectional view of the irradiation window provided in the electron beam irradiation apparatus.

On a wall 36a that is attached to the disinfection chamber 6 of the electron beam irradiation apparatus 2, an opening 36b is configured that substantially matches the opening 6b formed in the wall of the disinfection chamber 6, so that the emission window 44 is mounted. As illustrated in FIGS. 2-4, the emission window 44 includes a window mount 46 (an inner surface around the opening 36b of the vacuum room 40) that is attached around the periphery of the opening 36b on the inner wall of the accelerating tube 36, a window (window frame) 48 that is mounted on the front side of the window mount 46 (the disinfection room 30 side; it is positioned inside the disinfection chamber 6), and irradiation foil 52 that is fixed on the front face of the window 48 with a clamp member 50. In this embodiment, the window mount 46 is made of stainless steel, the window 48 is made of copper, and the clamp member 50 is made of stainless steel. Further, as for the irradiation foil 52, metal foil, such as titanium (Ti) foil, aluminum (Al) foil, and the like are used. Note that the material of these elements is not limited to the material mentioned above but any other metal can also be used.

The window 48 includes a plurality of electron beam transmission holes 54 that are divided by a plurality of crosspiece sections 48a. Electron beams that have passed through the opening 46a of the window mount 46 and the electron beam transmission holes 54 irradiate the interior of the disinfection room 30. Further, in this embodiment, part of the window mount 46 and the window 48, through which the electron beam emitted from the electron beam generator 34 passes through the irradiation window 44 into the disinfection room 30 being irradiated, is covered with carbon-fiber-reinforced plastic (CFRP) 56. The sections of FIG. 2 marked by thick lines are the carbon-fiber-reinforced plastic. The carbon-fiber-reinforced plastic may be provided as a plate member having thickness of about 0.5 mm-2.0 mm, and the plate may be fixed by bolting. Note that an adhesive or any other fastener may also be used instead of bolting. Although X-rays are generated when an electron beam strikes stainless steel or copper, the generated X-rays are significantly reduced when the metal surfaces are covered in such a manner with the carbon-fiber-reinforced plastic 56. Further, fluororesin of a certain thickness, which includes fluorine as the main element, may also be applied instead of the carbon-fiber-reinforced plastic 56. Furthermore, material including beryllium (Be) or nitrogen compound and the like may also be applied. Namely, in the present embodiment, the generation of X-rays is controlled by covering a surface of a metallic member that is irradiated by an electron beam (in this embodiment, the surfaces of the inner walls of the window mount 46 and the electron beam transmission holes 54 of the opening 46a and the window 48) with material including a chemical element (s) having an atomic number less than or equal to 10 as the main element, or material including at least one of the above-mentioned chemical elements as its main composition. However, an appropriate thickness is required for each material according to the intensity of an electron beam, so that a material without adequate thickness is not applied.

The beam catcher 32 may also be made of metals such as stainless steel or aluminum so that it generates X-rays when struck by irradiated electron beams. Therefore, the surface of the beam catcher 32 may be also covered with the material including either carbon-fiber-reinforced plastic (CFRP), fluorine or the like.

Although the embodiment of the present invention has been described herein with reference to the accompanying drawings, obviously many modifications and changes may be made by those skilled in this art without departing from the scope of the invention.

The present disclosure relates to subject matter contained in Japanese Patent Application No. 2012-042203 (filed on Feb. 28, 2012), which is expressly incorporated herein, by reference, in its entirety.

The invention claimed is:

1. An electron beam irradiation apparatus, comprising:
a vacuum room with a wall comprising lead and having an opening for irradiating an electron beam, an internal atmosphere of said vacuum room being evacuated;
an electron beam generator that is provided inside said vacuum room;
a window frame that is attached to and surrounds said opening of said vacuum room;
an irradiation foil fixed in said window frame through which an electron beam generated in said vacuum room is transmitted;
a disinfection chamber surrounded by walls comprising lead, connected to said vacuum room, and surrounding said irradiation foil;
a transfer system provided inside said disinfection chamber and transferring containers irradiated by the electron beam; and
at least an area of a surface of said window frame exposed to said vacuum room, being covered with carbon-fiber-reinforced plastic.

2. The electron beam irradiation apparatus according to claim 1, wherein a beam catcher for receiving an irradiated electron beam is provided on an opposite side of said irradiation foil with respect to an irradiated object and a surface of said beam catcher is covered with carbon-fiber-reinforced plastic.

3. The electron beam irradiation apparatus according to claim 1, wherein a surface of an inner wall about said opening of said vacuum room is covered carbon-fiber-reinforced plastic.

4. The electron beam irradiation apparatus according to claim 1, wherein said window frame comprises copper and an area of said window frame facing inside said vacuum room is covered with said carbon-fiber-reinforced plastic.

5. The electron beam irradiation apparatus according to claim 1, wherein said window frame is provided with a plurality of crosspiece sections aligned in parallel along one direction and each opposing surface of said crosspiece sections is covered with said carbon-fiber-reinforced plastic.

6. The electron beam irradiation apparatus according to claim 1, wherein said carbon-fiber-reinforced plastic reduces generation of X-rays.

7. The electron beam irradiation apparatus according to claim 1, wherein a thickness of said fiber-reinforced plastic is about 0.5 mm-2.0 mm.

8. The electron beam irradiation apparatus according to claim 1, wherein said carbon-fiber-reinforced plastic is fixed to the surface of said window frame by bolting.

9. The electron beam irradiation apparatus according to claim 1, wherein said carbon-fiber-reinforced plastic is fixed to the surface of said window frame by an adhesive.

* * * * *